(12) United States Patent
Kenknight et al.

(10) Patent No.: US 6,878,111 B2
(45) Date of Patent: *Apr. 12, 2005

(54) SYSTEM FOR MEASURING SUBJECTIVE WELL BEING

(75) Inventors: Bruce H Kenknight, Maple Grove, MN (US); Scott Thomas Mazar, Inver Grove Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 252 days.

This patent is subject to a terminal disclaimer.

(21) Appl. No.: 10/193,549

(22) Filed: Jul. 9, 2002

(65) Prior Publication Data

US 2004/0010184 A1 Jan. 15, 2004

(51) Int. Cl.⁷ .................................................. A61B 5/00
(52) U.S. Cl. ....................... 600/300; 178/920; 178/903; 607/60
(58) Field of Search ................................ 600/300–301, 600/513, 558, 559, 800; 128/903, 904, 920–925, 897–898; 607/27, 60–62; 705/1–4; 340/573; 434/236, 262

(56) References Cited

U.S. PATENT DOCUMENTS

| | | | | |
|---|---|---|---|---|
| 5,435,324 A | | 7/1995 | Brill | |
| 6,080,106 A | * | 6/2000 | Lloyd et al. | 600/300 |
| 6,190,313 B1 | * | 2/2001 | Hinkle | 600/300 |
| 6,282,441 B1 | * | 8/2001 | Raymond et al. | 600/513 |
| 6,361,501 B1 | * | 3/2002 | Amano et al. | 600/500 |
| 6,453,201 B1 | * | 9/2002 | Daum et al. | 607/62 |

OTHER PUBLICATIONS

Deiner, E., et al., "Recent Findings on Subjective Well–Being," http://www.psych.uiue.edu/–ediener/hottopic/paper1.html, pp. 1–22 (Mar. 1997), (this article will be published in the *Indian Journal of Clinical Psychology*, vol. 24, pp. 25–41.

* cited by examiner

Primary Examiner—Max F. Hindenburg
Assistant Examiner—Michael C Astorino

(57) ABSTRACT

A system for measuring subjective well-being utilizes an interactive communications module, an electronic transmission module and an intervention module. The interactive communications module receives data or input that reflects a person's subjective well-being and makes a temporal record of the input. The electronic transmission module transmits that data or input to a communications device. The intervention module is coupled to the interactive communications module to communicate a trend of subjective well-being. Trends may be created using a correlation module adapted to correlate and compare subjective and/or objective data. The correlation module may also include an inquiry module to allow a person to inquire about a person's subjective well-being.

20 Claims, 4 Drawing Sheets

US 6,878,111 B2

SYSTEM FOR MEASURING SUBJECTIVE WELL BEING

TECHNICAL FIELD

The present system relates generally to rehabilitative management systems and particularly, but not by way of limitation, to such a system for measuring and providing appropriate feedback of a person's subjective well-being.

BACKGROUND OF THE INVENTION

Subjective well-being (SWB) can be defined as the degree to which people have positive thoughts and feelings about their lives and are often measured through self-reports of life satisfaction. One currently popular measure of SWB is the Satisfaction with Life Scale (Pavot and Diener 1993), which asks individuals the extent of their agreement or disagreement on a seven-point scale with five statements regarding life satisfaction as shown below.

Using the 1–7 scale below, indicate your agreement with each item by placing the appropriate number on the line preceding that item. Please be open and honest in your responding.

7-Strongly agree
6-Agree
5-Slightly agree
4-Neither agree nor disagree
3-Slightly disagree
2-Disagree
1-Strongly disagree
   In most ways my life is close to my ideal.
   The conditions of my life are excellent.
   I am satisfied with my life.
   So far I have gotten the important things I want in life
   If I could live my life over, I would change almost nothing.

Other questionnaires are available to measure pleasant and unpleasant affect. For example, PANAS (Positive and Negative Affect Scale) is designed to separately measure both positive and negative affect. Development and validation of a brief measure of positive and negative affect: The PANAS scales. *Journal of Personality and Social Psychology*, 54, 1063–1070. This scale tends to measure aroused or activated states of affect (e.g., excitement and distress), and thus it might be preferable in some situations to use scales that measure a wider range of emotions (e.g., contentment and embarrassment). In addition to the above measures, a description of useful measures can be found in the prior art.

The assumption behind self-reports of SWB is that the respondent is in a privileged position to report his or her experience of well-being. Indeed, only the respondent can experience her or his pleasures and pains. Thus, self-report measures are critical and particularly appropriate in the field of rehabilitative management systems.

Self-report scales that are designed to measure SWB usually correlate with each other, and converge with SWB assessed by other methods. However, because of the potential shortcomings of self-report measures (e.g., response biases, memory biases, and defensiveness), researchers have worked to develop other ways of measuring SWB and protect the integrity of the data. For example, people's frequency of smiling, their ability to recall positive versus negative events from their lives are useful measures of SWB. In addition to the standard questionnaires that are well-known in the art, alternative methods based on self-reports such as interviews and the experience sampling method (mood reports collected at random moments over a period of weeks) have also been utilized. In addition, behavioral observations of affect expression in natural settings correlate with informant reports of emotion. Finally, electrophysiological measures also converge with self-reports of SWB. It is encouraging that measures based on diverse methodologies correlate and provide similar estimates of well-being because the multi-measure approach helps rule out artifactual explanations of the self-report data.

As discussed above, SWB is primarily defined in terms of the internal experience of the respondent. In its truest form, an external frame of reference is not imposed when assessing SWB. However, external frames of reference may be valuable in normalizing or correlating SWB data to events influencing groups or populations of individuals.

For example, researchers have found that all demographic factors together accounted for less than 20% of the variance in SWB. Variables such as education, ethnic status, and age often correlate at very low levels with reports of SWB. In addition, income in the U.S.A. correlates only about 12% with SWB. Thus, it seems that demographic variables such as age, education, sex, ethnicity and wealth often have weak relations to SWB.

Nevertheless, some demographic variables do consistently predict SWB. For example, married people of both sexes report more happiness than those who are never married, divorced, or separated. See Lee, G. R., Seccombe, K., & Shehan, C. L. (1991). Marital status and personal happiness: An analysis of trend data. *Journal of Marriage and the Family*, 53, 839–844. One benefit of marriage may be providing interesting and supportive social interactions for the individual. Furthermore, there is evidence that happy people are more likely to marry in the first place, so the causal influence between SWB and marriage may work in both directions. See Mastekaasa, A. (1992). Marriage and psychological well-being: Some evidence on selection into marriage. *Journal of Marriage and the Family*, 54, 901–911; Scott, C. K. (1991). In addition to the effects of marriage on participants, there are differences in SWB between the children of intact marriages versus divorced marriages. Life satisfaction is lower when one's parents had a highly conflictual marriage or when they were divorced, and this pattern is true in both individualistic and collectivistic cultures.

Another important area in assessing SWB is the distinction between on-line measures of well-being (at the moment) versus global reports of longer periods that are based on memory. If people's experiences over time are sampled randomly, a measure of their on-line levels of SWB can be obtained. Often pagers, alarm watches, or hand-held computers are used for the random experience sampling method to assess whether most of a person's moments are pleasant or unpleasant.

In sum, SWB attempts to understand people's self-evaluations of their lives. These evaluations may be primarily cognitive (e.g., when a person gives conscious evaluative judgments about his or her satisfaction with life as a whole, or evaluative judgments about specific aspects of his or her life such as perception of health) or might consist of the frequency with which people experience pleasant emotions (e.g., joy) and unpleasant emotions (e.g., depression). Furthermore, SWB is fairly consistent under most demographic variables. Thus, by obtaining a baseline measurement of a person's SWB, the medical practitioner can utilize that information as a positive reinforcement mechanism or to correlate the persons' SWB to objective medical data. In this way, SWB can serve as a rehabilitative management tool and might also serve as a predictive health management and assessment tool.

For these and other reasons, there is a need to provide a primary input system to assess a person's physical and emotional SWB that allows both a person and/or a medical practitioner to easily and quickly access the information. The system also must be capable of storing and correlating the information so the person and medical practitioner can observe trends of SWB. Finally, the input system must be easy to use and encourage compliance and data input, yet robust enough to provide useful data to the practitioner and the person.

SUMMARY

According to one aspect of the invention, there is provided a primary input system for a patient management system that stores and manipulates SWB data. Input can be accomplished in several ways. However, as with any measurement of SWB, the person is primarily responsible for entering the data. Based on the frequency of the person's input, the medical practitioner or other health care professional may use this frequency data to assess the value of the input. In other words, a person whose SWB is good might be prone to enter data more frequently than the ill-feeling person. However, depending on the psychological makeup of the person, the opposite may occur. In other words, a person that feels good might enter data less frequently than when he or she feels bad. In either event, the input system of the invention coupled with the ability to correlate the subjective input with objective medical data, will allow the medical practitioner to customize the value of each person's input. This provides the person and the medical practitioner with a reliable tool to assess a person's SWB without the need to engage in laborious, time-consuming testing and evaluation.

The invention may also provide the medical practitioner with a set of subjective data to which he can compare objective medical data. By way of a non-limiting example only, if objective medical data (as measured by a patient management device or obtained clinically) shows an improvement in cardio-function, that data can be compared to the person's subjective feeling of well-being and used as a predictive tool for the medical practitioner. Thus, aggregated well-being data can be correlated to objective medical data to create trends of overall health from both subjective and objective points of view.

A trend can be created by applying an algorithm to a series of data point values assigned to SWB input. By way of a non-limiting example, SWB input could be indexed to a set of numerical values such that good SWB and its sub-components might carry the values 1, 1.1, 1.2, etc. and neutral SWB and its sub-components might carry the values 2, 2.1, 2.2, etc. In this example, bad SWB and its sub-components might carry values of 3. In this way, SWB input could be compared to input frequency to create a temporal trend of SWB data. An interactive communications module could then communicate that trend to the patient or medical practitioner in various formats, like a pictorial or a graphical representation.

In one embodiment, the input system includes an implanted device. In this embodiment, the device may solicit the input of the person using an electrical or audible stimulus. Those skilled in the art will appreciate that such an implanted device can be calibrated to induce a physical response in the person, like a muscle twitch. The solicitation mechanism might include an audible prompt, like a series of audible signals (dots or dashes). In response to the prompt, the person would provide SWB data through electronic communication with the implanted device or verbally through a voice recognition program. In the embodiment of the invention capable of an audible prompt and/or receiving verbal input, the implanted device would include a built-in speaker and/or microphone. Data input of subjective well-being may be prompted by a device other than the implant, like an external electronic device.

In another embodiment of the implanted device, the primary input system includes a built-in accelerometer that measures the person's physical activity. This combined device would allow the primary input system to solicit input based on the person's physical activity as sensed by the accelerometer.

In yet another embodiment of the input system, the system includes a hand-held device external to the person that is adapted to receive telephonic, iconic, textural or tactile input. The input system could also include a personal computer or other personal computing device (i.e., hand-held PC or PDA) capable of receiving iconic, telephonic, textural or tactile input.

The person's SWB may also be prompted by computerized query. In this embodiment, the input system would query the person on his subjective well-being. Based on those queries, the person would then select categories of responses or respond in a free-style manner. Again, the input device might include a personal computing device.

In a further embodiment, the person's input can be accomplished through telephony. In this embodiment, the person's assessment of SWB would be recorded by a system that would convert the person's verbal assessment of well-being into a subjective well-being data set. Telephonic devices may also be used to prompt the input of data. By way of a non-limiting example only, the system might include an automatic dialing system that rings the person's telephone and prompts the person to enter SWB data.

Subjective well-being input may also be accomplished textually. In this embodiment, the person's SWB may be measured by textural prompts similar to Pavot and Diener's Satisfaction with Life scale. Input may also be accomplished by utilizing a combination of textural and iconic prompts. The input system in this embodiment might again include a personal computing system.

In yet a further embodiment, icons might represent categories of SWB. The icons may include virtual or physical buttons. An example of a virtual icon, while not limiting for the present invention, would be an icon that is activated by touching an LCD or other visually interactive active computerized device. A non-limiting example includes a personal computing system or touch-sensitive PDA.

The primary input system, if external to the person, might also register the tactile signature of the input. For example, in an embodiment that includes a series of physical buttons that represent SWB, the length of time the button is depressed and how hard it is depressed can be correlated to subjective and objective data to further assess the person's overall well-being. This tactile signature feature of the present invention may also serve as a stand-alone indicator of the person's subjective well-being. By way of a non-limiting example only, the tactile signature data can serve as independent, objective data to assist in creating a customized profile of the person's SWB. In this embodiment, the primary input system might include a touch-sensitive keypad device.

In a preferred embodiment, input is accomplished through a series of icons that generally represent a person's SWB. By way of a non-limiting example only, a happy face can be utilized to indicate the person is feeling good. A neutral face may be selected if the person's SWB is neutral. In addition, the person may select a frowning face to indicate that his SWB is poor. Each of these general icons might also include sub-icons or menus that further define the person's SWB. By way of a non-limiting example only, if the person selects the frowning face icon, a sub-menu of more specific icons might be presented to the person to help further define the person's feelings. In addition, icons representing the person's emotional state can be utilized to differentiate between physical impairments and emotional distress. Thus, the sub-menu of icons might include a face with a tear to connote that the person's SWB relates more to a poor emotional state than a physical ailment. Another sub-menu icon might represent self-abuse by the person. In this non-limiting example, the sub-menu icon might include a liquor bottle to indicate that the persons' poor SWB was caused by overindulgence or abuse of chemical substances or alcohol.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claims.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION OF PREFERRED EMBODIMENTS OF THE PRESENT INVENTION

In the following detailed description, reference is made to the accompanying drawings that form a part hereof, and in which is shown by way of illustration specific embodiments or examples. These embodiments may be combined, other embodiments may be utilized, and structural, logical, and electrical changes may be made without departing from the spirit and scope of the present invention. The following detailed description is, therefore, not to be taken in a limiting sense, and the scope of the present invention is defined by the appended claims and their equivalents.

The present system is described with respect to a primary input system for measuring and manipulating SWB data. The term "primary input system" refers to a system adapted to receive SWB information as input data. The system can then store, collate and correlate the input data and generate feedback 109, 111 on subjective well-being to the person and/or the medical practitioner. This feedback 109, 111 collectively and/or separately includes an intervention module. The storage, collating and correlating include, but is not limited to, a temporal record of the input. The term "subjective well-being" or "SWB" refers to the psychological principle of allowing the person to subjectively measure his or her physical and/or emotional state through the primary input system.

As used in the present invention, the terms data, input and information are essentially synonymous in describing the person's assessment of SWB and the feedback 109, 111 generated by that assessment through the primary input system or other communications device.

Figure 1:
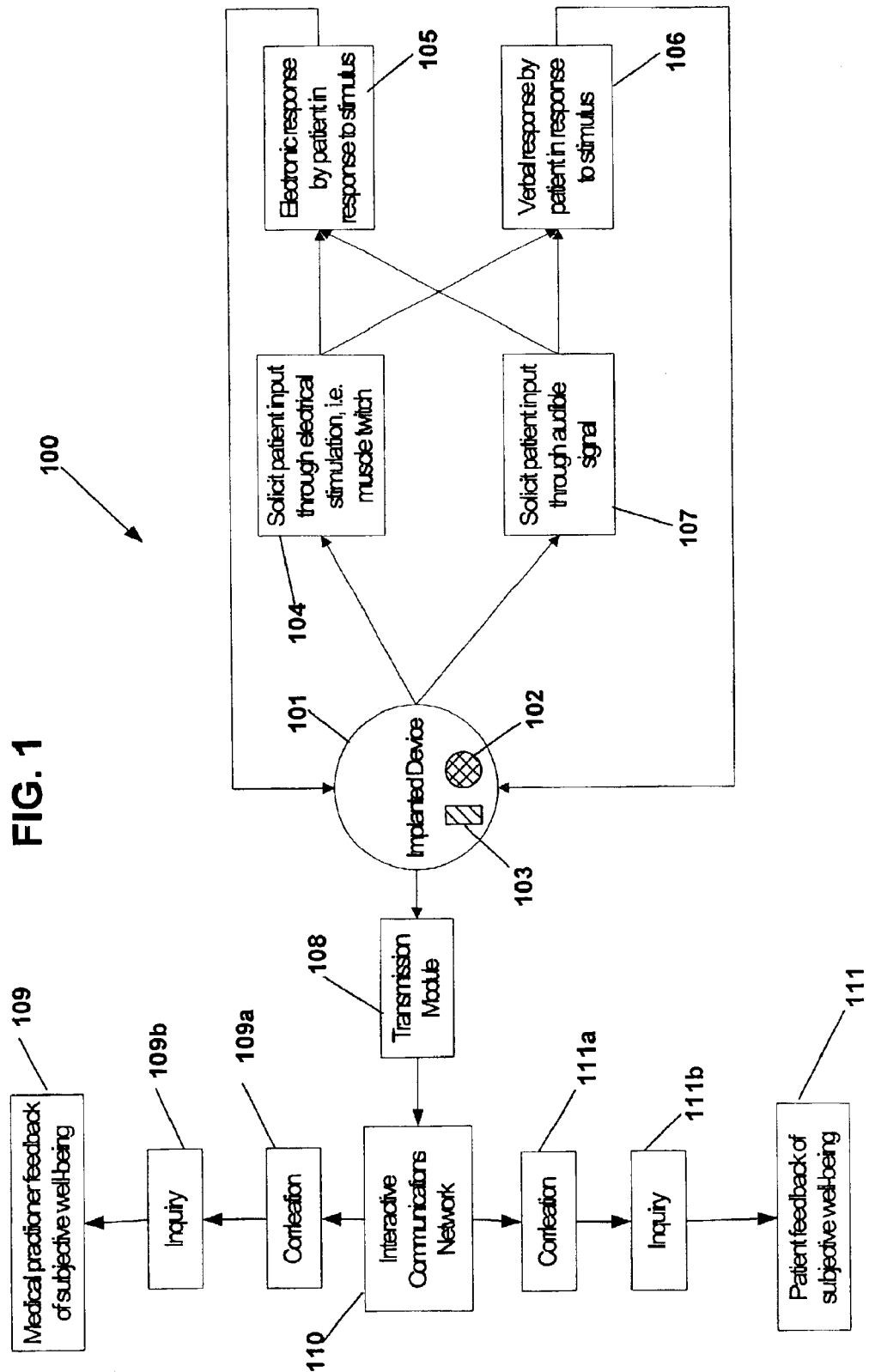
FIG. 1 is a schematic/block diagram illustrating generally, among other things, one embodiment of the primary input system of the present invention.

FIG. 1 is a schematic/block diagram illustrating generally one embodiment of a primary input system 100 utilizing an implanted device 101 that serves as an interactive communications module. In this embodiment, the implanted device 101 solicits input from a person through an electrical stimulus 104. This stimulus 104 might include an electrical stimulus to a person's muscle. When the muscle is stimulated in this manner and the person recognizes this through an electrically induced muscle twitch, it would prompt the person to respond with SWB input. The SWB input might include an electronic response 105 or a verbal response 106.

If prompted for an electronic response 105, the person may enter SWB data through a device in electronic communication with the implanted device 101. Such a device might include any device capable of electronic communication using standard communications protocols, like digital or cellular communication or an RF protocol like Bluetooth™.

If prompted for a verbal response 106 by the person, the person may verbally respond to the implanted device by using structured statements that correspond to different levels of SWB. By way of a non-limiting example only, the person may respond by saying "good" or "okay" or "bad" to reflect his or her SWB. From this point, the person may utilize other structured statements to further define his or her SWB. By way of a non-limiting example only, the person, in addition to saying that he is having a "bad" day, might also saying that he is "sad" to distinguish between a physical ailment and a poor emotional state. By further non-limiting example, the verbal response 106 might include the use of voice recognition software that converts a free-style response like "I feel great" into a finite category or categories of SWB data. In this embodiment, the implanted device 101 might include a microphone/speaker 102 to capture and record the person's verbal response 106.

In another embodiment shown in FIG. 1, the implanted device 101 might solicit input from the person through an audible signal 107. In this embodiment, and by way of a non-limiting example only, the audible signal 107 might include a series of short beeps (dots) or longer beeps (dashes). The audible signal 107 of this embodiment would prompt the person to respond electronically 105 or verbally 106. As with the embodiment that includes electrical stimulation, the person may respond electronically or verbally in the same manner.

In another embodiment shown in FIG. 1, an accelerometer 103 might cause the implanted device 101 to solicit SWB input through an electrical stimulus 104 or audible signal 107. In this embodiment, and by way of a non-limiting example only, the accelerometer 103 is an integral part of the implanted device 101 and measures the physical activity of the person. Based on that measurement, the implanted device 101 then decides whether it should prompt the person for SWB data. By way of a non-limiting example only, if the accelerometer 103 records little movement by the person at a time when such movement is expected (i.e., during waking hours), the accelerometer 103 in communication with the implanted device 101 will cause it to prompt the person, either electronically or verbally, for SWB information. As with the aforementioned embodiments, the person may respond either electronically 105 or verbally 106 in the same manner.

With either an electrical or verbal response by the person, the response is relayed to a transmission module 108 by the implanted device 101 as shown in FIG. 1. The transmission module 108 might include an integral part of the implanted device 101 or include a separate device. In either embodiment, the transmission module's 108 purpose is to transmit SWB information to an interactive communications network 110.

The interactive communications network 110 in turn relays the SWB data to an intervention module 109, 111 for access by a medical practitioner and/or a patient. In order for the medical practitioner or patient to inquire about the SWB data received by the interactive communications network 110, the primary input system 100 might further include correlation modules 109a, 111a and inquiry modules 109b, 111b to correlate a trend of SWB data or correlate SWB data to objective medical data and to allow the medical practitioner and patient to access SWB data.

By way of a non-limiting example only, the correlation module 109a, 111a may include algorithms that access SWB and/or objective medical data for comparative purposes. For example, a patient's SWB input for a series of days shows good SWB. This data is then compared to data obtained from the accelerometer 103, which shows the patient has been very active during the same period. Thus, a customized SWB profile for this patient tends to show a strong positive correlation between SWB and physical activity. As the databases of subjective and objective data increase, the patient or practitioner may access the primary input system 100, through the inquiry module 109b, 111b, to obtain a historical view of the patient's physical activity. Using algorithms, the patient physical activity may be charted against SWB data. In this way, the patient or practitioner may easily recognize a correlated trend in physical activity and SWB.

Figure 4:
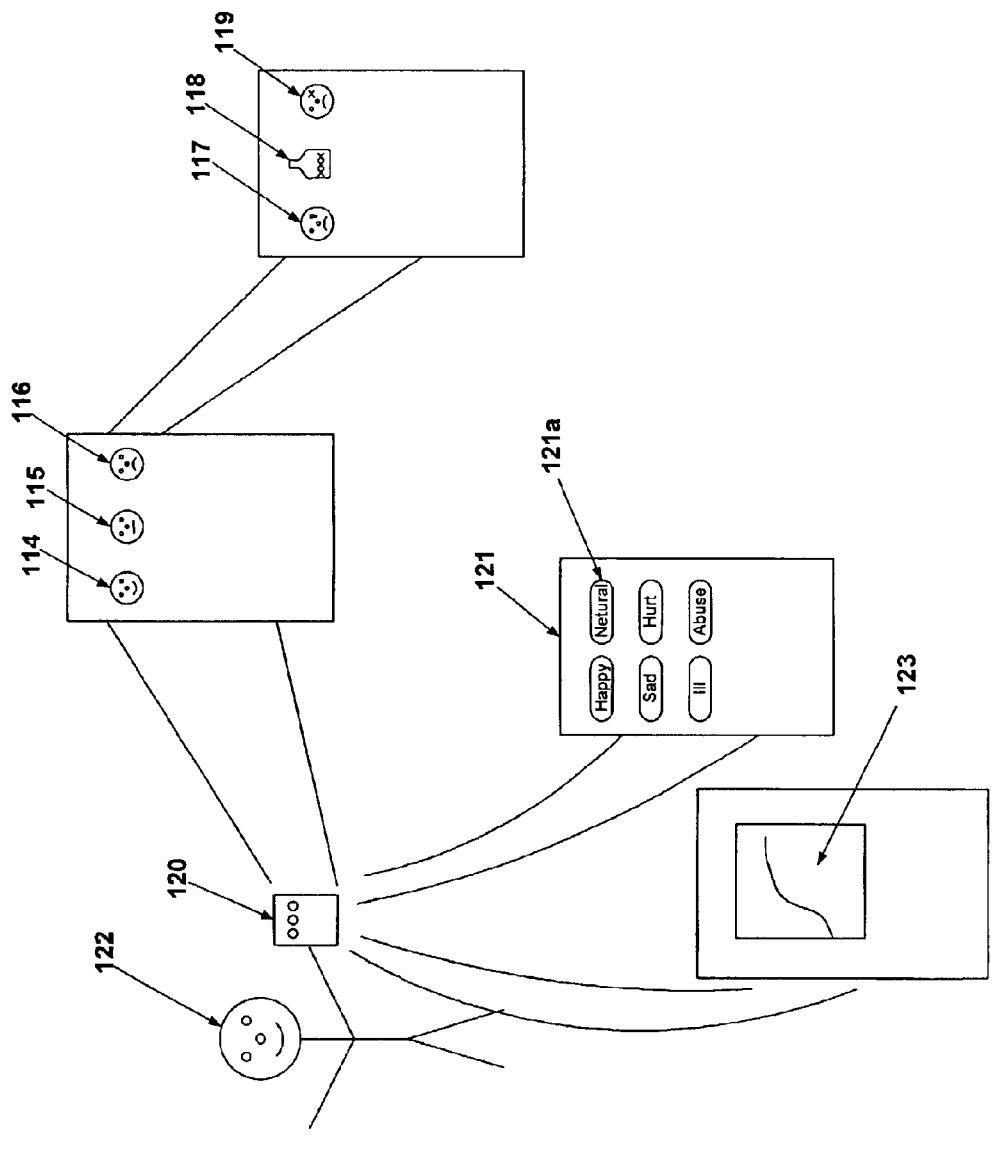
FIG. 4 is a schematic/block diagram illustrating generally, among other things, another embodiment of the primary input system of the present invention.

In the embodiment shown in FIG. 4, the medical practitioner or patient 122 may access and view SWB trend data via a personal computing device 120. The device 120 could be configured to allow the medical practitioner or patient a view trend data in a graphical format 123.

The correlation 109a, 111a and inquiry modules 109b, 111b might be an integral part of the interactive communications network 110. The interactive communications network 110 might also be an integral part of either the implanted device 101 and/or the transmission module 108 and/or the intervention module 109, 111. The interactive communications network 110 might also include a system external to the person, but easily accessible by the person or the medical practitioner. By way of a non-limiting example only, the interactive communications network 110 might include a global computer network.

Figure 2:
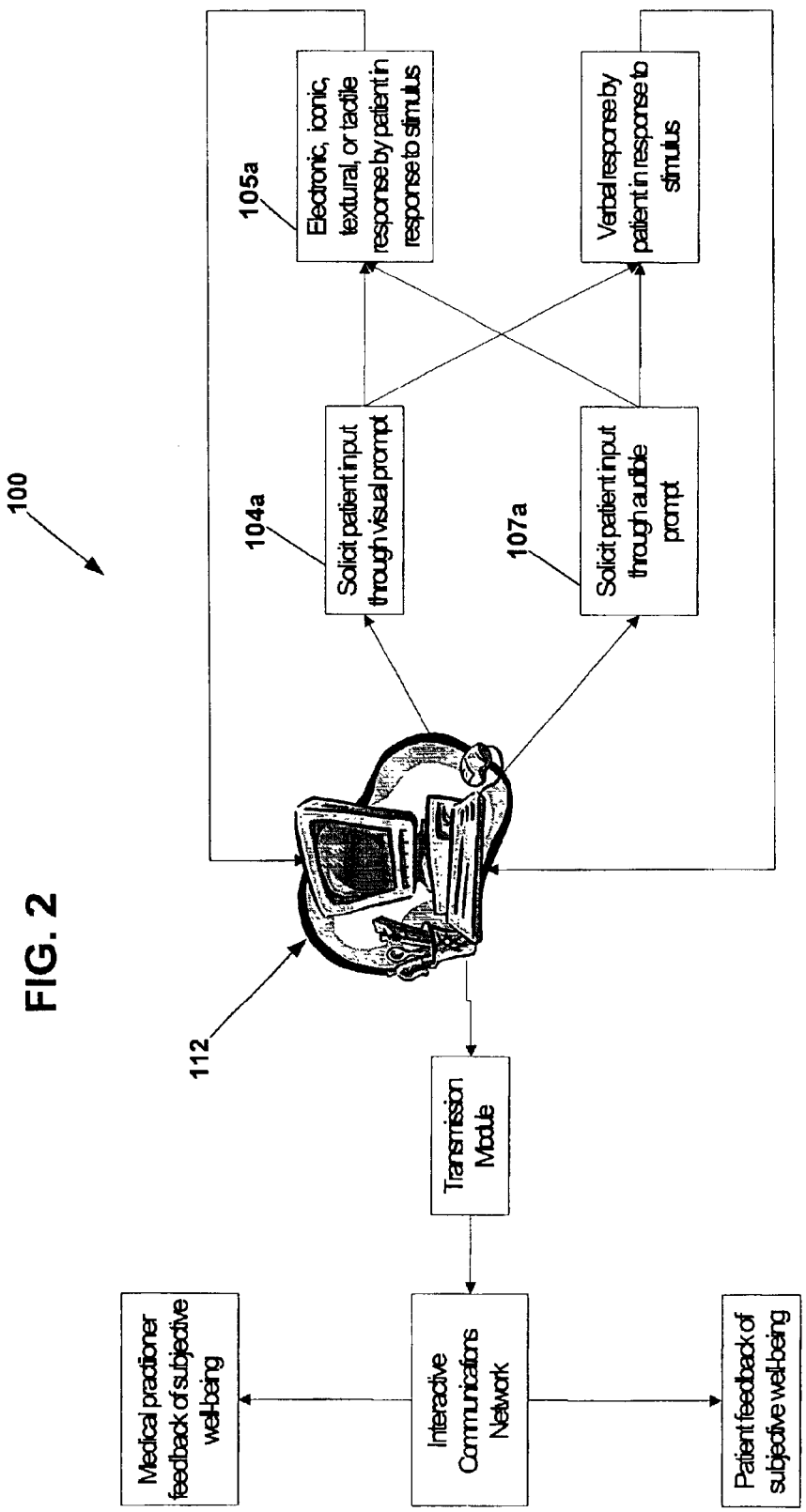
FIG. 2 is a schematic/block diagram illustrating generally, among other things, another embodiment of the primary input system of the present invention.

FIG. 2 is a schematic/block diagram illustrating generally another embodiment of the primary input system 100 utilizing a personal computing device 112 as the interactive communications module. In this embodiment, the personal computing device 112 might include a personal computer or hand-held device like a Personal Digital Assistant (PDA). In this embodiment, the primary input system 100 may prompt the person for SWB input through an audible 107a or visual prompt 104a generated by the personal computing device 112. The personal computing device 112 may also be in electronic communication with an implanted device 101 that in turn provides an electrical stimulus 104 to the person to prompt the person's input of SWB data. Because of the inherent versatility of a personal computing device 112, it may be adapted to receive telephonic, iconic, textural or tactile SWB information 105a.

In the embodiment shown in FIG. 2, tho person could enter SWB data textually by responding to textural prompts similar to Pavot and Diener's Satisfaction with Life scale. Such prompts may also be communicated to the person through icons 114–119 (FIG. 4) or a combination of text and icons 114–119.

By way of a non-limiting example only, the personal computing device 112 may prompt the person to enter SWB information through a query system. In this embodiment, the input system would query the person on his subjective well-being. Based on those queries, the person may select categories of responses or respond in a free-style manner. As with the aforementioned embodiments, SWB data is transmitted to the personal computing device 112, which can include an integrated or separate component of the transmission module 108 and/or interactive communications network 110.

Figure 3:
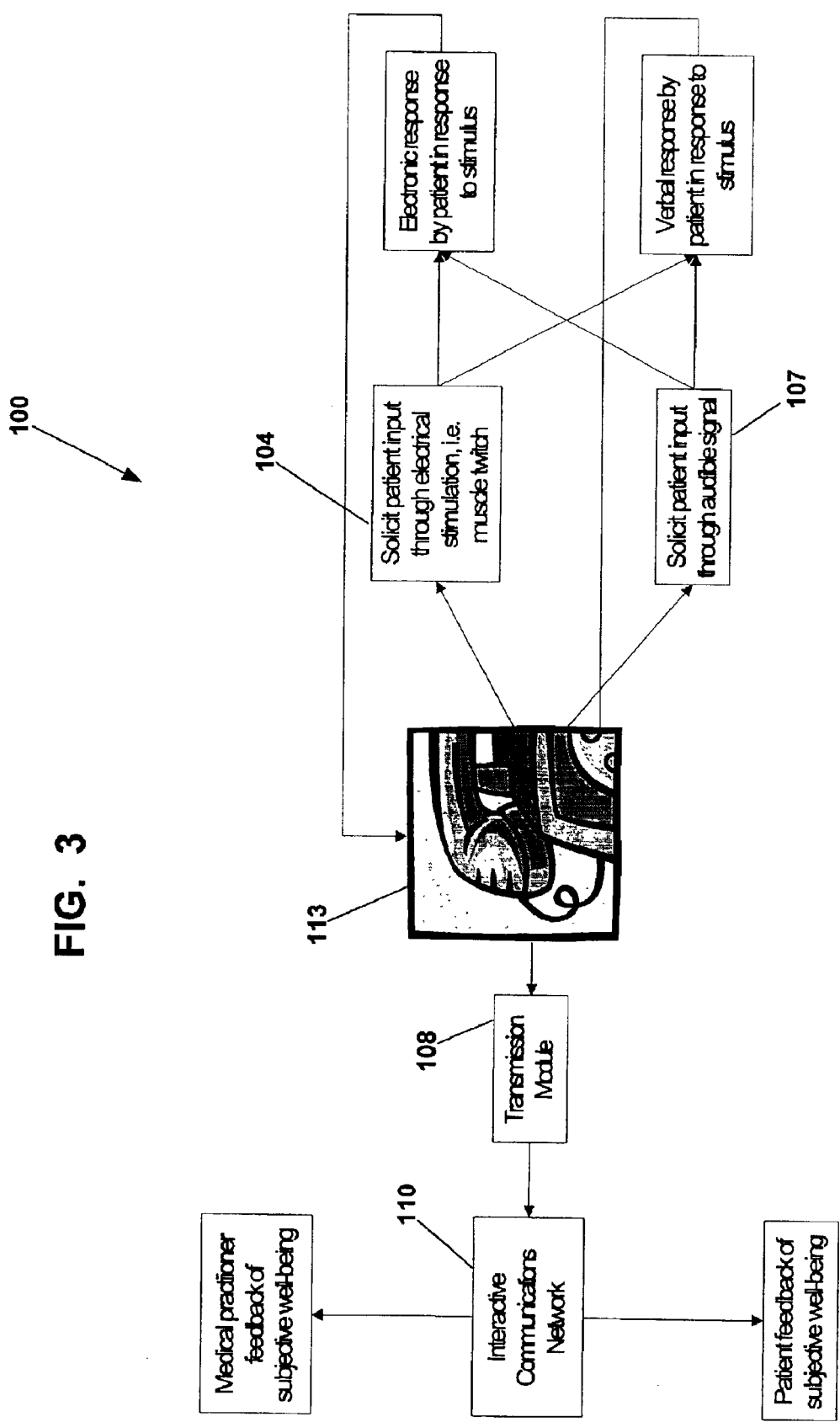
FIG. 3 is a schematic/block diagram illustrating generally, among other things, another embodiment of the primary input system of the present invention.

FIG. 3 is a schematic/block diagram illustrating generally another embodiment of the primary input system 100 utilizing a telephonic device 113 as the interactive communications module. In this embodiment, the telephonic device 113 might include a wired or wireless telephone. In this embodiment, the primary input system 100 might prompt the person for SWB input through an audible signal 107 generated by the telephonic device 113. By way of a non-limiting example only, the system might incorporate an automatic dialing system that rings the person's telephone and prompts the person to enter SWB data. In other words, the primary input system 100 may call the person through the telephonic device 113. In this embodiment, the telephonic device 113 would record the person's assessment of subjective well-being and convert it into a SWB data set. The telephonic device 113 may also be in electronic communication with an implanted device 101 that in turn provides an electrical stimulus 104 to the person to prompt the person's input of SWB data. As with the aforementioned embodiments, SWB data is transmitted to the telephonic device 113, which can include an integrated and/or separate component of the transmission module 108 and/or interactive communications network 110.

FIG. 4 are screen shots 114–119 of the primary input system utilizing a personal computing device 120 as the interactive communications module. In this embodiment, the personal computing device 120 includes a hand-held device like a PDA. The personal computing device 120 displays a series of icons 114–119 that generally represent a person's subjective well-being. For example, a happy face 114 can be utilized to indicate the person is feeling good. A neutral face 115 may be selected if the person's SWB is neutral. In addition, the person may select a frowning face 116 to indicate that his SWB is poor.

The icons might be virtual or physical buttons. An example of a virtual icon, while not limiting for the present invention, would be an icon that is activated by touching an LCD or other visually interactive active computerized device. The primary input system 112 or 120, if external to the person, may also register the tactile signature of the person's input. For example, in an embodiment that includes a series of physical buttons 121a that represent SWB, the length of time the button 121a is depressed and how hard it is depressed can be correlated to subjective and objective data to further assess the person's overall well-being. This tactile signature feature of the present invention may also serve as a stand-alone indicator of a person's subjective well-being. By way of a non-limiting example only, the tactile signature data can serve as independent, objective data to assist in creating a customized profile of the person's SWB. In this embodiment, the primary input system might include a touch-sensitive keypad device 121.

Each of the general icons 114–116 might also incorporate sub-icons or menus that further define the person's subjective well-being. By way of a non-limiting example only, if the person selects the frowning face icon 116, a sub-menu of more specific icons 117–119 may be presented to the person to help farther define the person's feelings. In addition, icons representing the person's emotional state 117 can be utilized to differentiate between physical impairments 119 and emotional distress. By way of a non-limiting example only, the sub-menu of icons might include a face with a tear 117 to connote that the person's SWB relates more to a poor emotional state than a physical ailment 119. Another sub-menu icon 118 might represent self-abuse by the person. In this non-limiting example, the sub-menu icon 118 might be represented by a liquor bottle 118 to indicate that the persons' SWB of poorness was caused by overindulgence or abuse of alcoholic beverages.

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

What is claimed is:

1. A system for subjectively measuring a person's physical and/or emotional well-being, the system comprising:
   a. an implanted interactive communications module adapted to receive data that reflects a person's subjective well-being;
   b. an interactive electronic transmission module coupled to the interactive communications module to transmit the data to a communications device; and
   c. an intervention module coupled to the interactive communications module to communicate a trend of subjective well-being.

2. The primary input system of claim 1, wherein the system further comprises a correlation module that correlates the person's input to create a trend of subjective well-being.

3. The primary input system of claim 1, wherein the system further comprises a correlation module that correlates the person's input to create a trend of subjective well-being and further correlates the input with objective data on the person's well-being to create a comparative trend of subjective well-being data to objective well-being data.

4. The correlation module of claim 2 wherein the correlation module further comprises an inquiry module.

5. The correlation module of claim 3 wherein the correlation module further comprises an inquiry module.

6. The interactive communications module of claim 1, wherein the interactive communications module makes a temporal record of the person's input.

7. The interactive communications module of claim 1, wherein the interactive communications module automatically prompts the person to enter subjective well-being data.

8. The interactive communications module of claim 7, wherein the prompt is an electrically induced.

9. The interactive communications module of claim 8, wherein the electrically induced prompt induces a physical response in the person.

10. The interactive communications module of claim 9, wherein the physical response in the person comprises a muscle twitch.

11. The interactive communications module of claim 7, wherein the prompt is audibly induced.

12. The interactive communications of module of claim 1, wherein the interactive communications module comprises an accelerometer.

13. The interactive communications of module of claim 1, wherein the representation of the person's subjective well-being comprises a verbal response.

14. The interactive communications of module of claim 1, wherein the representation of the person's subjective well-being comprises an electronic response.

15. The electronic response of claim 14, wherein the response is entered through a device in electronic communication with the interactive communications module.

16. The interactive communications of module of claim 1, wherein the interactive communications module comprises a global computer network.

17. The interactive electronic transmission module of claim 1, wherein the representation of the person's subjective well-being comprises a plurality of icons.

18. The icons of claim 17, wherein the icons comprise a happy face, a straight face, and a frowning face.

19. The icons of claim 18, wherein the happy face connotes a good subjective well-being indicator, the straight face connotes a neutral subjective well-being indicator, and the frowning face connotes a bad subjective well-being indicator.

20. The icons of claim 19, wherein the happy face icon further comprises a sub-menu of icons that connote varying degrees of relative good subjective well-being, the straight face icon further comprises a sub-menu of icons that connote varying degrees of relative neutral subjective well-being, and the frowning face further comprises a sub-menu of icons that connote varying degrees of relative bad subjective well-being.

* * * * *